(12) United States Patent  
Nordin et al.

(10) Patent No.: US 9,047,499 B2  
(45) Date of Patent: Jun. 2, 2015

(54) ANTI-COUNTERFEITING METHODS

(71) Applicant: Panduit Corp., Tinley Park, IL (US)

(72) Inventors: Ronald A. Nordin, Naperville, IL (US); Masud Bolouri-Saransar, Orland Park, IL (US)

(73) Assignee: Panduit Corp., Tinley Park, IL (US)

( * ) Notice: Subject to any disclaimer, the term of this patent is extended or adjusted under 35 U.S.C. 154(b) by 0 days.

(21) Appl. No.: 13/905,354

(22) Filed: May 30, 2013

(65) Prior Publication Data

US 2013/0320079 A1 Dec. 5, 2013

Related U.S. Application Data

(60) Provisional application No. 61/654,521, filed on Jun. 1, 2012.

(51) Int. Cl.

| | |
|---|---|
| G06F 17/00 | (2006.01) |
| G06K 19/00 | (2006.01) |
| G06K 19/06 | (2006.01) |
| G06F 7/04 | (2006.01) |
| G06K 5/00 | (2006.01) |
| G06Q 30/00 | (2012.01) |
| G06K 19/07 | (2006.01) |
| G06Q 50/22 | (2012.01) |
| G06Q 10/08 | (2012.01) |
| G06F 19/00 | (2011.01) |

(52) U.S. Cl.  
CPC .............. *G06K 5/00* (2013.01); *G06Q 30/0185* (2013.01); *G06K 19/0723* (2013.01); *G06Q 50/22* (2013.01); *G06Q 10/087* (2013.01); *G06Q 10/0832* (2013.01); *G06F 19/3462* (2013.01)

(58) Field of Classification Search  
CPC ............ G06K 19/0723; G06Q 10/087; G06Q 30/0185  
USPC ........... 235/375, 385, 487, 492; 340/5.8, 10.1  
See application file for complete search history.

(56) References Cited

U.S. PATENT DOCUMENTS

| | | |
|---|---|---|
| 6,226,619 B1 | 5/2001 | Halperin et al. |
| 6,738,903 B1 | 5/2004 | Haines |
| 6,883,710 B2 | 4/2005 | Chung |
| 6,996,543 B1 | 2/2006 | Coppersmith et al. |
| 7,395,963 B2 | 7/2008 | Silverbrook et al. |
| 7,543,745 B1 | 6/2009 | Simske et al. |
| 7,581,242 B1 | 8/2009 | Oget et al. |

(Continued)

OTHER PUBLICATIONS

RFiD Journal "Small Tech Firm Seeks Fees From Pharma," 2 pages, Jun. 22, 2005.

(Continued)

*Primary Examiner* — Thien M Le  
*Assistant Examiner* — Claude J Brown  
(74) *Attorney, Agent, or Firm* — Christopher S. Clancy; Yuri Astvatsaturov (57) ABSTRACT

The present invention relates to the field of product authentication and anti-counterfeiting techniques, and more specifically, to techniques employing RFID tags and encryption technologies. Embodiments of the present invention illustrate the use of RFID tags having encrypted information stored therein which upon decryption by a down-stream entity or an end user can help determine the authenticity of a product. Furthermore, the embodiments disclosed herein illustrate various examples supply chains and private key management.

8 Claims, 8 Drawing Sheets

(56) References Cited

U.S. PATENT DOCUMENTS

| | | | |
|---|---|---|---|
| 7,606,557 B2* | 10/2009 | Park et al. ............... 455/410 |
| 7,664,257 B2 | 2/2010 | Hohberger et al. |
| 8,001,016 B2 | 8/2011 | Balinsky et al. |
| 8,037,294 B2 | 10/2011 | Nochta |
| 8,040,244 B2 | 10/2011 | Bauchot et al. |
| 8,058,973 B2 | 11/2011 | Zeng et al. |
| 8,112,626 B1 | 2/2012 | Adler et al. |
| 2003/0234718 A1* | 12/2003 | Fujisawa et al. ............ 340/5.1 |
| 2005/0234823 A1* | 10/2005 | Schimpf ...................... 705/50 |
| 2005/0289061 A1* | 12/2005 | Kulakowski et al. .......... 705/50 |
| 2006/0174129 A1 | 8/2006 | Brignone et al. |
| 2007/0106897 A1* | 5/2007 | Kulakowski ................ 713/171 |
| 2008/0024268 A1* | 1/2008 | Wong et al. ................. 340/5.8 |
| 2008/0046263 A1* | 2/2008 | Sager et al. ..................... 705/1 |
| 2008/0106372 A1* | 5/2008 | Chang ......................... 340/5.8 |
| 2008/0191882 A1* | 8/2008 | Zhou et al. ................ 340/572.4 |
| 2009/0040023 A1* | 2/2009 | Pretorius .................... 340/10.1 |
| 2009/0096574 A1* | 4/2009 | Oberle ......................... 340/5.8 |
| 2009/0169019 A1 | 7/2009 | Bauchot et al. |
| 2009/0267729 A1 | 10/2009 | Rowe et al. |
| 2010/0019026 A1* | 1/2010 | Hochfield et al. ............ 235/375 |
| 2010/0033300 A1* | 2/2010 | Brandin ....................... 340/5.8 |
| 2010/0073147 A1* | 3/2010 | Guajardo Merchan et al. .......................... 340/10.51 |
| 2010/0134287 A1* | 6/2010 | Lettieri ..................... 340/572.1 |
| 2010/0140344 A1 | 6/2010 | Toofan et al. |
| 2011/0225064 A1* | 9/2011 | Fou ............................ 705/26.41 |
| 2011/0283369 A1* | 11/2011 | Green ............................ 726/30 |
| 2012/0218077 A1* | 8/2012 | de Velasco Cortina et al. .......................... 340/5.74 |
| 2012/0290841 A1* | 11/2012 | Jentzsch ...................... 713/168 |

OTHER PUBLICATIONS

"From Identification to Authentication—A Review of RFID Product Authentication Techniques," Lehtonen, et al., 17 pages, Jan. 1, 2006.

\* cited by examiner

ANTI-COUNTERFEITING METHODS

CROSS-REFERENCE TO RELATED APPLICATIONS

This application claims the benefit of U.S. Provisional Patent Application No. 61/654,521, filed on Jun. 1, 2012, which is incorporated herein by reference in its entirety.

FIELD OF INVENTION

The present invention relates to the field of product authentication and anti-counterfeiting techniques, and more specifically, to techniques employing RFID tags and encryption technologies.

BACKGROUND

Product counterfeiting is a worldwide problem. Many different industries are affected by counterfeiting, including the pharmaceutical, electronics and telecommunication, apparel and fashion, and music and film industries. Today's counterfeit goods have a broad range and often include prescription drugs, electronic equipment, watches, and fashion accessories. Counterfeiters have become so advance, that virtually any product on the market can fall prey. While in cases such as fashion and apparel, a fake product may translate into a general sense of dissatisfaction for the end-user, in cases of pharmaceutical drugs, the consequences of a fake drug may be more dire. Rarely, if ever, are counterfeit drugs manufactured under any health and safety standards. Worse yet, those making the fake drugs often use placebo-type or harmful ingredients to pass off the goods as genuine. Such practices can lead to severe medical problems or death for unsuspecting users, and contribute to a rise in human drug resistance. Similarly, inferior counterfeit electronic or infrastructure equipment can lead to catastrophic failures. As one example, inferior communication cables or cable ties used in an aircraft can be the cause of irreversible malfunctions while in mid-flight.

Certain anti-counterfeiting techniques have been proposed and implemented to some extent. These include 1D and 2D bar codes utilizing national database inquires to validate products; Radio-Frequency Identification (RFID) Tags utilizing national database inquires to validate products; covert techniques that utilize wireless tags embedded within plastic molded caps or packaging that utilize national database inquires to validate products; and other covert technologies (e.g., "micro-labeling", embedded images, holographic images, nano-labeling technologies) utilizing difficult-to-copy labeling or tagging techniques (these could also involve inquires into a national database).

However, these techniques are either relatively easy to duplicate, difficult to manufacture (hence leading to higher cost), and/or make it hard for the customer to determine the authenticity of the products. Therefore, there exists the need for improved methods, systems, and apparatuses to guard against counterfeiting.

SUMMARY

To better understand the present invention, it is important to understand the mechanisms by which counterfeit products can be introduced into the supply chain and the market place. The supply chain of a typical prescription drug will be used as a non-limiting example. The chain usually starts at the original equipment manufacturer (OEM) pharmaceutical manufacturer (e.g., Pfizer, Johnson & Johnson, Abbott, Baxter, or others), where a particular product is manufactured. The product is then usually shipped to a wholesale distributer, who then distributes it to various pharmacies. Finally, the pharmacies sell or otherwise distribute the product directly to the end-customers. Note that in this scenario, as in many others, there are a handful of original product manufacturers, a larger number of wholesale distributors, likely thousands of retailers (in this case pharmacies), and ultimately millions of end-users.

Figure 1:
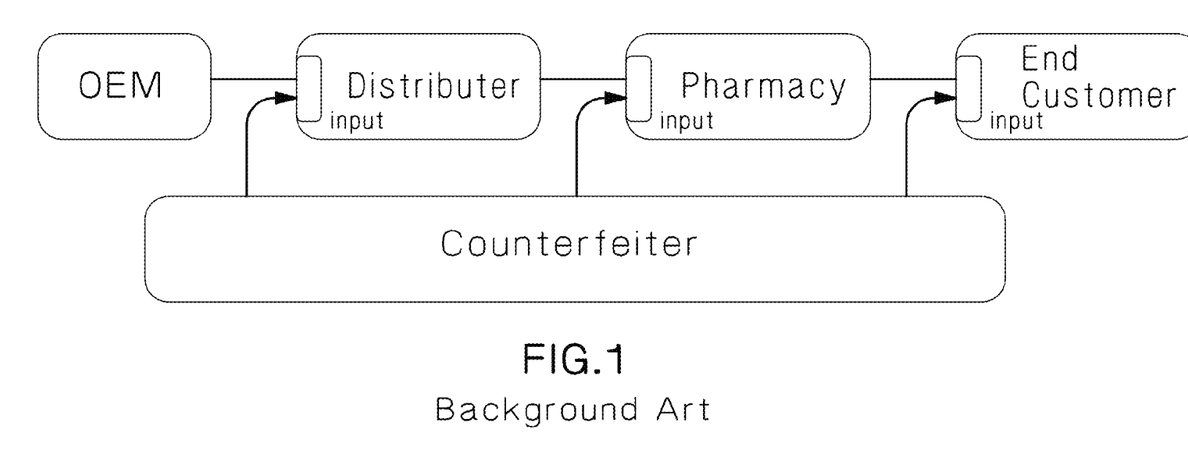
FIG. 1 shows an exemplary product supply chain with counterfeiters entering said chain.

As illustrated in FIG. 1, counterfeit drugs often enter the supply chain prior to the distributor, the pharmacy, or the end-customer. These counterfeit products can be difficult to authenticate as the sophistication of the counterfeiters increases. Once a counterfeit product penetrates the supply chain, the ability to determine that product's authenticity becomes even harder. While a thorough product inspection can be done when products enter one of the facilities as described above, these inspection techniques can often be impractical for each of the facilities within the supply chain.

Accordingly, the present invention discloses methods and systems directed to prevention of counterfeiting and product authentication.

In one embodiment, the present invention is an anti-counterfeiting method using RFID and encryption technologies.

In another embodiment, the present invention is a method of managing private and public encryption and decryption keys across a supply chain.

In yet another embodiment, the present invention is a method of managing private and public encryption and decryption keys across a supply chain when multiple OEM facilities are involved.

In yet another embodiment, the present invention is a method of incorporating secure supply chain information into product identifiers/labels/tags.

In yet another embodiment, the present invention is a method against counterfeiting, where the method includes the steps of: providing a radio-frequency identification (RFID) tag capable of being attached to a product, the RFID tag having a unique identification string hardcoded therein and a user-accessible memory; asymmetrically encrypting by way of a private encryption key the unique identification string to obtain an authentication code word; writing the authentication code word into the user-accessible memory; reading the authentication code word from the user-accessible memory via an RFID reader; decrypting the authentication code word using a public decryption key to obtain a decrypted result; and comparing the decrypted result to the unique identification code, where if the decrypted result matches the unique identification code, the product is genuine, and if the decrypted result does not match the unique identification code, the product is counterfeit.

In yet another embodiment, the present invention is a method against counterfeiting in a supply chain having a plurality of original equipment manufacturer (OEM) entities, each of the OEM entities manufacturing a plurality of units of a respective product. The method includes providing a plurality of radio-frequency identification (RFID) tags, each of the RFID tags having a unique identification string hardcoded therein and a user-accessible memory. The method also includes having a process-controlling entity: asymmetrically encrypt by way of a private encryption key each of the unique identification strings to obtain respective authentication code words, each of the respective authentication code words corresponding to one of the respective unique identification strings; write each of the respective authentication code words into respective one of the user-accessible memory;

divide the plurality of RFID tags into a plurality of batches, each of the plurality of batches having a respective plurality of OEM RFID tags, each of the plurality of batches corresponding to one of the plurality of OEM entities; and respectively distribute the plurality of batches to the plurality of OEM entities. The method also includes having each of the plurality of OEM entities: attach each of the respective plurality of OEM RFID tags to one of the plurality of units of the respective product; and place the plurality of units of the respective product into the supply chain, the supply chain including at least one of a distributer and a retail location. The method also includes reading at least one authentication code word and at least one respective unique identification code from at least one respective RFID tag attached to at least one respective unit, the reading occurring via an RFID reader at at least one of the distributer and the retail location. The method also includes decrypting the read at least one authentication code word using a public decryption key to obtain a decrypted result. And the method also includes comparing the decrypted result to the read at least one respective unique identification code, where if the decrypted result matches the read at least one respective unique identification code, the at least one respective unit is genuine, and if the decrypted result does not match the read at least one respective unique identification code, the at least one respective units is counterfeit.

In yet another embodiment, the present invention is a method against counterfeiting in a supply chain having a plurality of original equipment manufacturer (OEM) entities, each of the OEM entities manufacturing a plurality of units of a respective product. The method includes having a process-controlling entity manage a plurality of private encryption keys, each of the plurality of private encryption keys having a respective public decryption key, each of the plurality of private encryption keys corresponding to one of the plurality of OEM entities. The method also includes providing a plurality of respective radio-frequency identification (RFID) tags to each of the plurality of OEM entities, each of the RFID tags having a unique identification string hardcoded therein and a user-accessible memory. The method also includes having each of the plurality of OEM entities: asymmetrically encrypt by way of the respective private encryption key each of the respective unique identification strings to obtain respective authentication code words, each of the respective authentication code words corresponding to one of the respective unique identification strings; write each of the respective authentication code words into respective one of the user-accessible memory; attach each of the plurality of respective RFID tags to one of the plurality of units of the respective product; and place the plurality of units of the respective product into the supply chain, the supply chain including at least one of a distributer and a retail location. The method also includes reading at least one authentication code word and at least one respective unique identification code from at least one respective RFID tag attached to at least one respective unit, the reading occurring via an RFID reader at at least one of the distributer and the retail location. The method also includes decrypting the read at least one authentication code word using one of the respective public decryption keys to obtain a decrypted result. And the method also includes comparing the decrypted result to the read at least one respective unique identification code, where if the decrypted result matches the read at least one respective unique identification code, the at least one respective unit is genuine, and if the decrypted result does not match the read at least one respective unique identification code, the at least one respective units is counterfeit.

These and other features, aspects, and advantages of the present invention will become better-understood with reference to the following drawings, description, and any claims that may follow.

DETAILED DESCRIPTION

The following description will be directed towards embodiments of the present invention used in connection with prescription drugs. However, it should be understood that these embodiments are non-limiting and the disclosed methods, systems, and apparatuses may be used in a wide range of applications where prevention of counterfeiting and product authentication is desired. It should also be noted that as used herein, the terms "anti-counterfeiting," "prevention of counterfeiting," and "product authentication" are not mutually exclusive and may be used synonymously. Likewise, as used herein, the terms "counterfeit," "fake," and "non-authentic" are not mutually exclusive and may be used synonymously.

Accordingly, in one embodiment, the present invention employs asymmetric encryption together with RFID tags to enable product authentication. The RFID tags generally include a coded word written into the user writable memory area of an RFID tag. This coded word uses asymmetric encryption techniques, and is derived from the unique ID of the RFID tag itself (note that in other embodiments, one could concatenate the unique RFID tag ID number with an identifier of the product as well (e.g., a serial number) to create the coded word). These asymmetric encryption keys can be varied over time for an additional layer of security. In this manner, the counterfeiting of a product (which includes authentication means) can be extremely difficult and the determination of a product's authenticity can be easily made via an RFID reader and a calculation (either embedded within the reader, or in an external processor or by a hand calculation).

The underlying encryption technique used in connection with the present invention is commonly referred to as asymmetric public key cryptography. In general terms, this technique employs two keys, a private key (that is kept securely at the manufacturing site) that encrypts a data string and a public key (meaning easily and openly available to the industry) that can be used only to decrypt the data string to validate the product's authenticity. The algorithm used to produce a coded word by encrypting a data string is asymmetric in that the public can only decipher code words and they cannot create code words.

Figure 2:
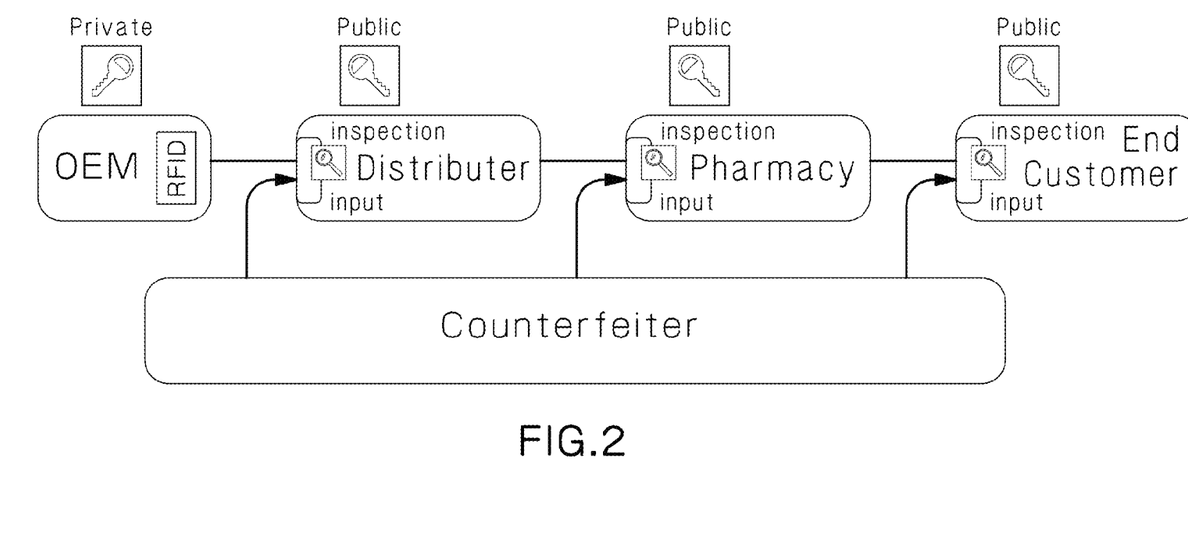
FIG. 2 shows a supply chain according to one embodiment of the present invention.
Figure 3:
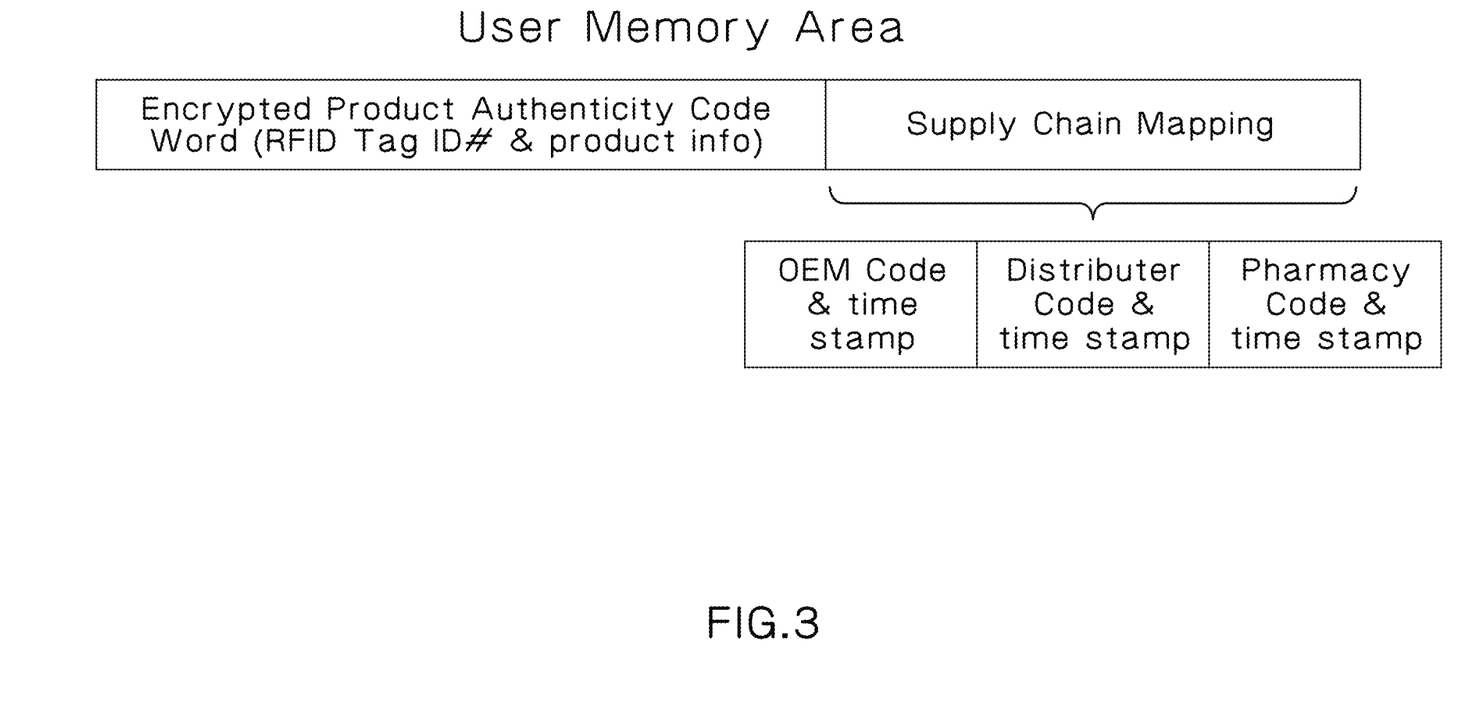
FIG. 3 shows an RFID memory map in accordance with an embodiment of the present invention.

A supply chain with an integrated anti-counterfeiting and inspection process according to one embodiment of the present invention is illustrated in FIG. 2. In this process, RFID tags are programmed and mounted onto the product packaging at an OEM site. The programming of the tags includes the encryption process through the use of a private key. Optionally, tamper-proof RFID tags can be used, where if the tag is removed from the package, the tag is disabled via a variety of techniques. As the finished products leave the OEM manufacturing facility and enter the supply chain, downstream facilities augment their incoming product inspection process with an RFID reader that is capable of de-ciphering the coded string through the use of an available public key. Once the string is deciphered, manual or automated authentication is performed. After authentication has been performed, the downstream facilities can optionally update the RFID tag with appropriate information that the product reached a particular facility correctly (e.g., facility ID#, time stamp, inventory personal, etc.) as illustrated in FIG. 3. In one embodiment, the updated information is electronically written into a password-protected area of the RFID tag. In this manner, all downstream facilities can authenticate the product in a similar fashion and optionally verify that the product went through the supply chain correctly.

Figure 4:
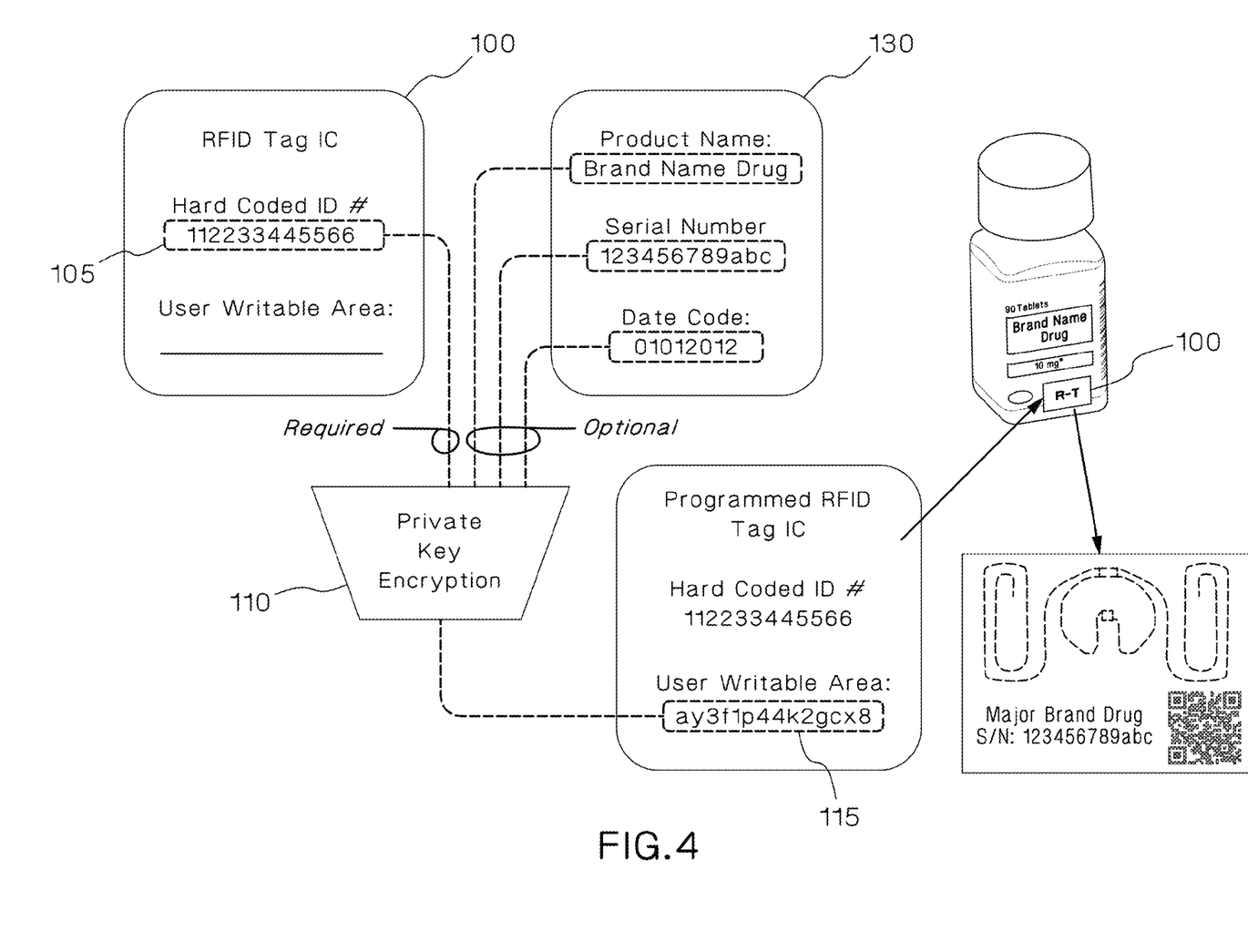
FIG. 4 shows an encryption process in accordance with an embodiment of the present invention.

Turning back to the programming of RFID tags at an OEM site, FIG. 4 illustrates a general overview of this process. An RFID tag 100 has a unique identification string (ID#) 105 integrated (or "hard-coded") into the silicon of the integrated circuit (IC) of the RFID tag. For an EPC Gen2 (abbreviation for EPCglobal UHF Class 1 Generation 2) compatible tag, the unique ID# is 36 bits long. This ID# is part of the IC and cannot be readily changed or modified. Additionally, user-memory space (the length of which varies from vendor to vendor of RFID tags) can be used to electronically store additional information. In some embodiments, this user-space can be further protected by a 32 bit password, which increases the security of the tag. It is in this area that an encrypted Authentication Code Word (ACW) can be inserted. The read-only unique ID# contained in the RFID tag IC is encrypted using a private key 110 to generate an ACW 115 and the ACW 115 is then written into the user memory area of the RFID tag 100 IC.

To authenticate a product, the information contained in the RFID tag is read using a conventional RFID reader, the ACW is decrypted using the publicly known key, and the result thereof is compared to the unique ID# of the RDIF tag (or, as noted previously, to the unique ID# concatenated with an identifier of the product if such combination is used during the original encryption). If a match occurs, then the product could be said to be authentic. On the other hand, if there is a mismatch, the product in question could be said to be counterfeit. A product counterfeiter likely lacks the ability to create their own fake RFID tags because they do not have the private key that allows them to encrypt the RFID tags ID# and store the corresponding ACW in the user-memory area. Furthermore, the counterfeiter would almost certainly be unable to copy existing RFID tags and replicate them because the RFID ICs have unique code strings embedded therein. While there is a possibility that a counterfeiter can manufacture their own RFID tags, the likelihood of such occurrence is relatively low.

In other embodiments, additional security features can be incorporated into the present invention. For example, the RFID IC's user-memory can be configured for "write-only" access, preventing the ability to delete or modify information that has already been written; restricting the valid range of RFID tag ID#s used in connection with a certain product or a certain product segment; utilizing a national database to enable inquires on valid non-duplicated RFID ID#'s; periodically changing private encryption keys; incorporating additional product, time line, or supply chain information into the user-memory space; or any combination thereof.

Figure 5:
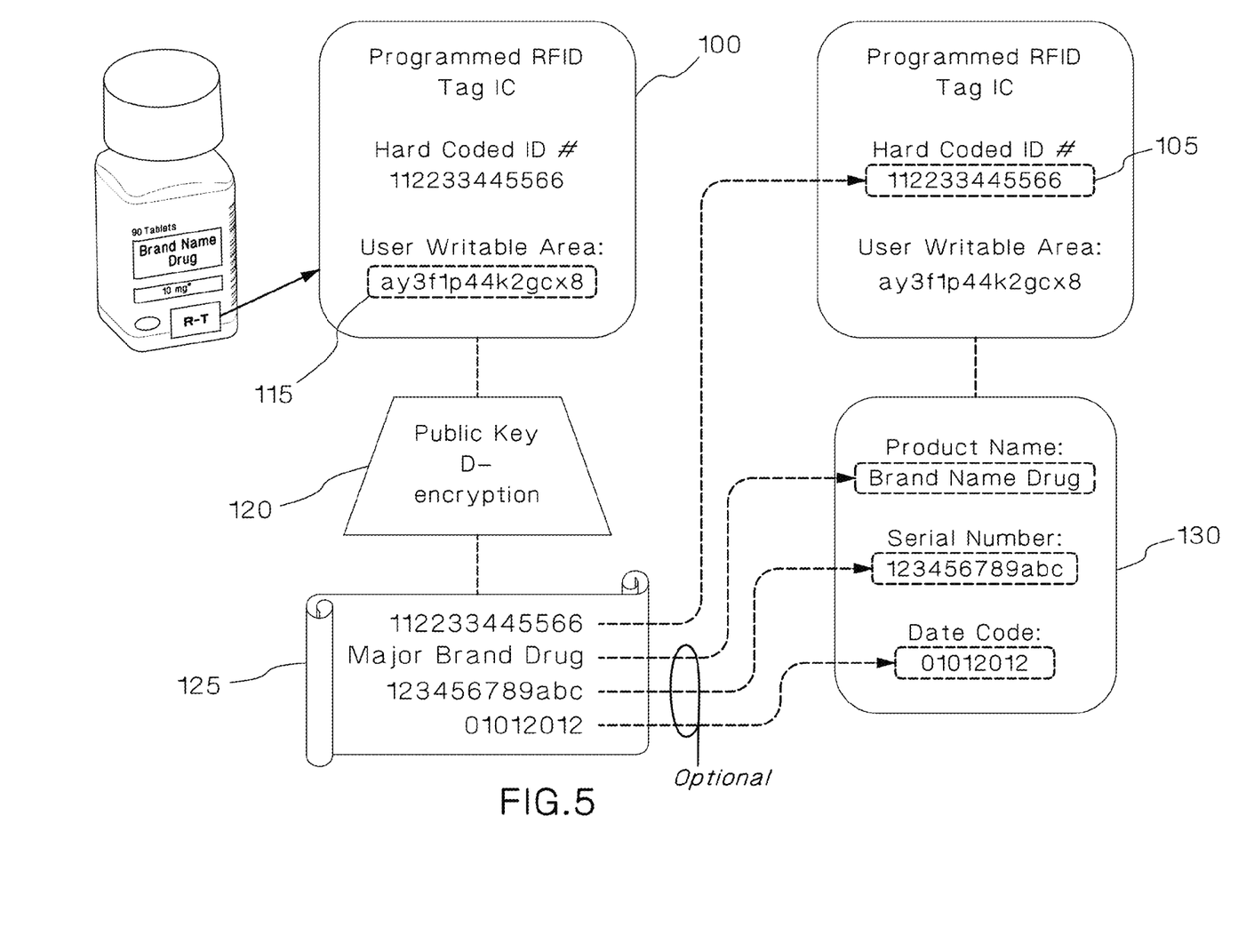
FIG. 5 shows a decryption and authentication process in accordance with an embodiment of the present invention.
Figure 6:
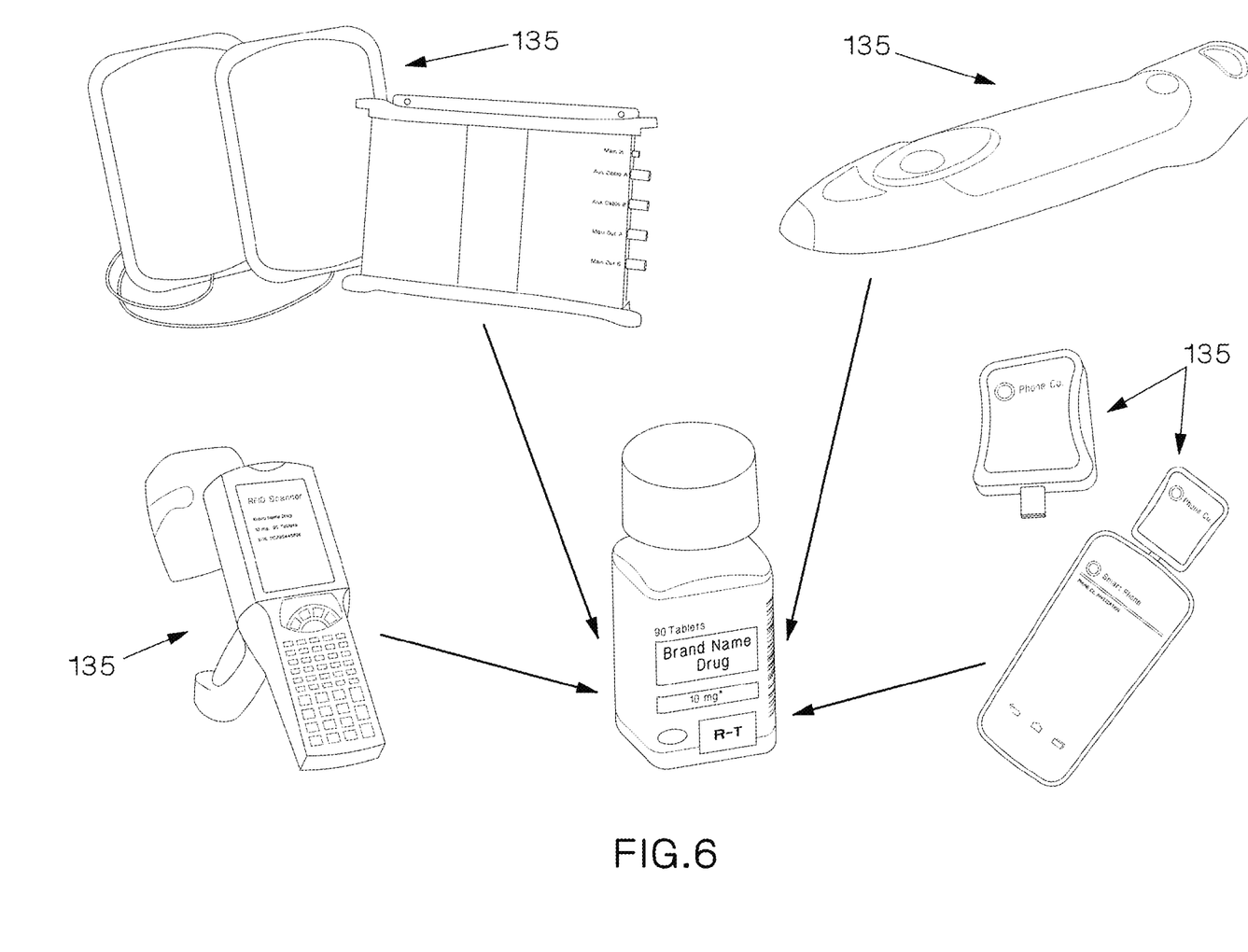
FIG. 6 shows some embodiments of RFID readers which may be used in accordance with the present invention.
Figure 7:
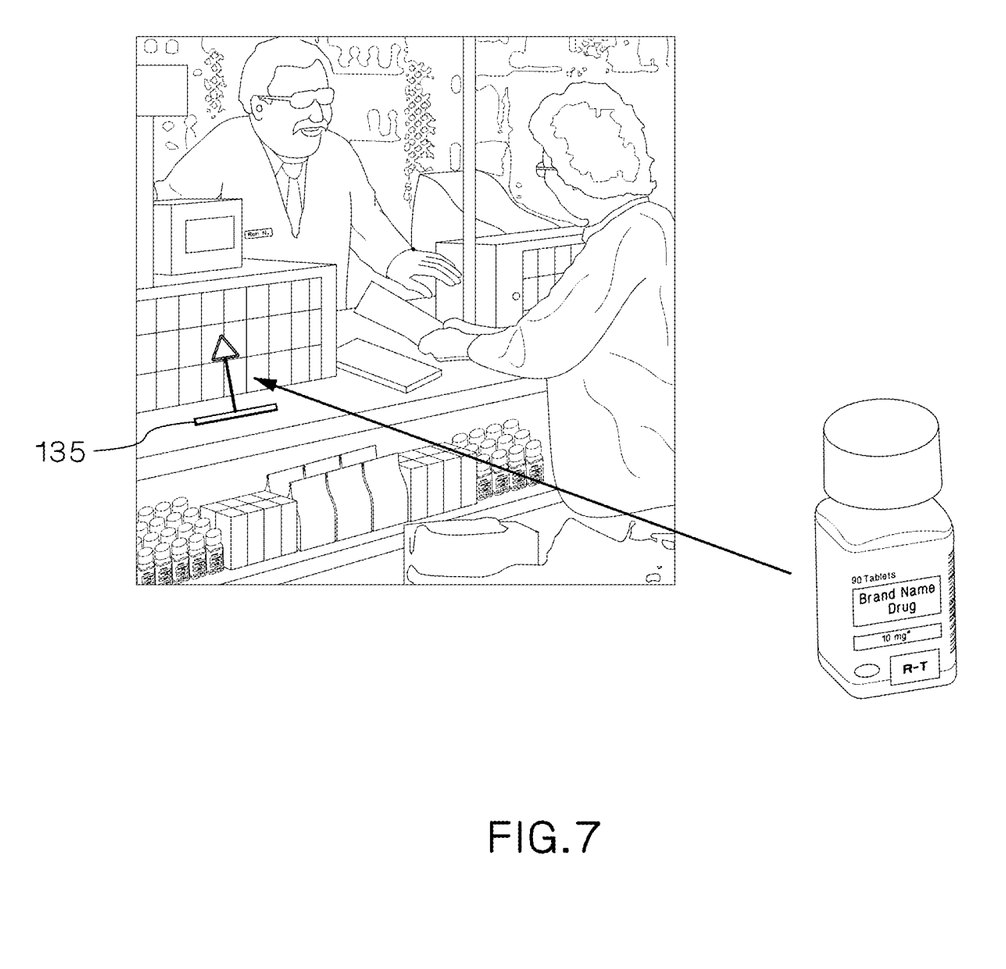
FIG. 7 shows an embodiment of the present invention for use by the end-consumer.

A general outline of the decryption and authentication process is illustrated in FIG. 5. Here, the product-receiving facility uses the publicly available key 120 to decrypt the ACW 115 stored in the user-memory of an RFID tag 100 and then matches the output 125 to the RFID's unique ID# 105 as well as any additional relevant product information 130 such as manufacturer's name, serial number, manufacture/expiration date, and any other information that may have been encoded originally into the ACW 115. Furthermore, if supply chain information has been written into the RFID tag as the product has passed from point to point within the chain, this information can be used for further verification of products and of proper channels of distribution. In an embodiment of the present invention, a UHF RFID reader is used to obtain the unique ID#, the ACW, and any other information electronically stored in the RFID tag, and submit that information to a software application. Relying on the publicly available key, the software application decrypts the ACW and compares the results to the unique ID# and any other identifying information which may have been used originally to encode the ACW. In an embodiment, the software application operates on a workstation separate from the RFID reader. In a variation of this embodiment, the software application may be web-based and made available to the user by internet/intranet means. In another embodiment, the software application is integrated into the RFID reader. In yet another embodiment, the RFID reader is a portable device adapted for use by a human. In yet another embodiment, the RFID reader is a part of an automated system. In yet another embodiment, the RFID reader 135 is linked to the software application at least in part by wireless means. FIG. 6 illustrates some embodiments of an RFID reader that can be used in accordance with the present invention. Any one of these or similar types of RFID readers can optionally be made available in pharmacies for use by the end-user. One embodiment of an RFID reader 135 at a pharmacy is illustrated in FIG. 7.

In other embodiments of the present invention, the ACW can be attached or associated with a particular product by additional means. For example, it can be alphanumerically printed on the product itself or on the packaging of the component (e.g., a bag that a product is contained in); it can be presented as a bar code printed on the part itself or on its packaging; it can be electronically stored within the part (if the part is so capable of); or any combination thereof. In any of these embodiments, the RFID tags containing a unique ID# would still be affixed to the product or product packaging.

Furthermore, the present invention is not limited to electronic means of decrypting the ACW, and in other embodiment the ACW may be decrypted manually by a publicly available algorithm.

In certain embodiments, such as those where there is more than one OEM manufacturer, it may be desirable to limit the distribution of the private key among various manufacturers, or otherwise provide some foam of tracking in case a breach of the private key occurs.

Figure 8:
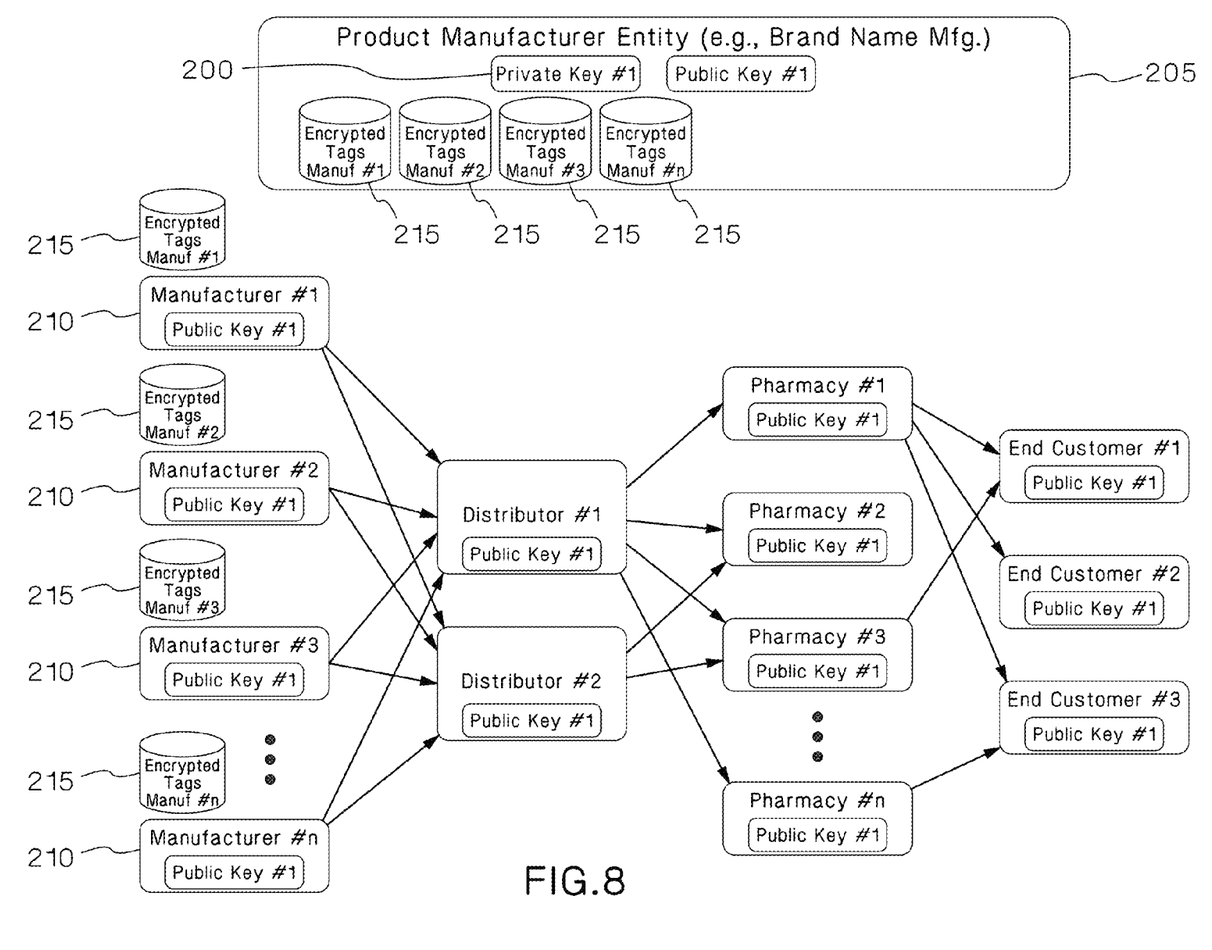
FIG. 8 shows a supply chain map according to an embodiment of the present invention where there is more than one OEM manufacturer.

One such embodiment is illustrated in FIG. 8. In this case, a single private key 200 is kept within the process-controlling product-manufacturing entity 205. This single entity provides to each of the OEM manufacturers 210 a set of product RFID tags 215 with the encryption data already written into the user memory. Alternatively, the process-controlling product-manufacturing entity provides an authenticity table (that provides the ACW with the appropriate RFID Tag's ID#) which contains the planned month's worth of products production's based on planned production information. In this fashion the OEM manufacturers only have the planned month's worth of production's authenticity codes, and if a breech in security occurs at one of the manufacturers, only one month's worth of production only from one type of manufacturer may be compromised. An alternative technique would be to provide the authenticity table via a secure website for the manufacturers in which they can, in real time, obtain the ACW to be written into the RFID tag's user memory. Yet another alternative technique would be to provide the manufacturer with a secure website so that the manufacturers can, in real time, supply the RFID tag's ID# and in return obtain a corresponding ACW that should be stored into the RFID tag's user memory.

Figure 9:
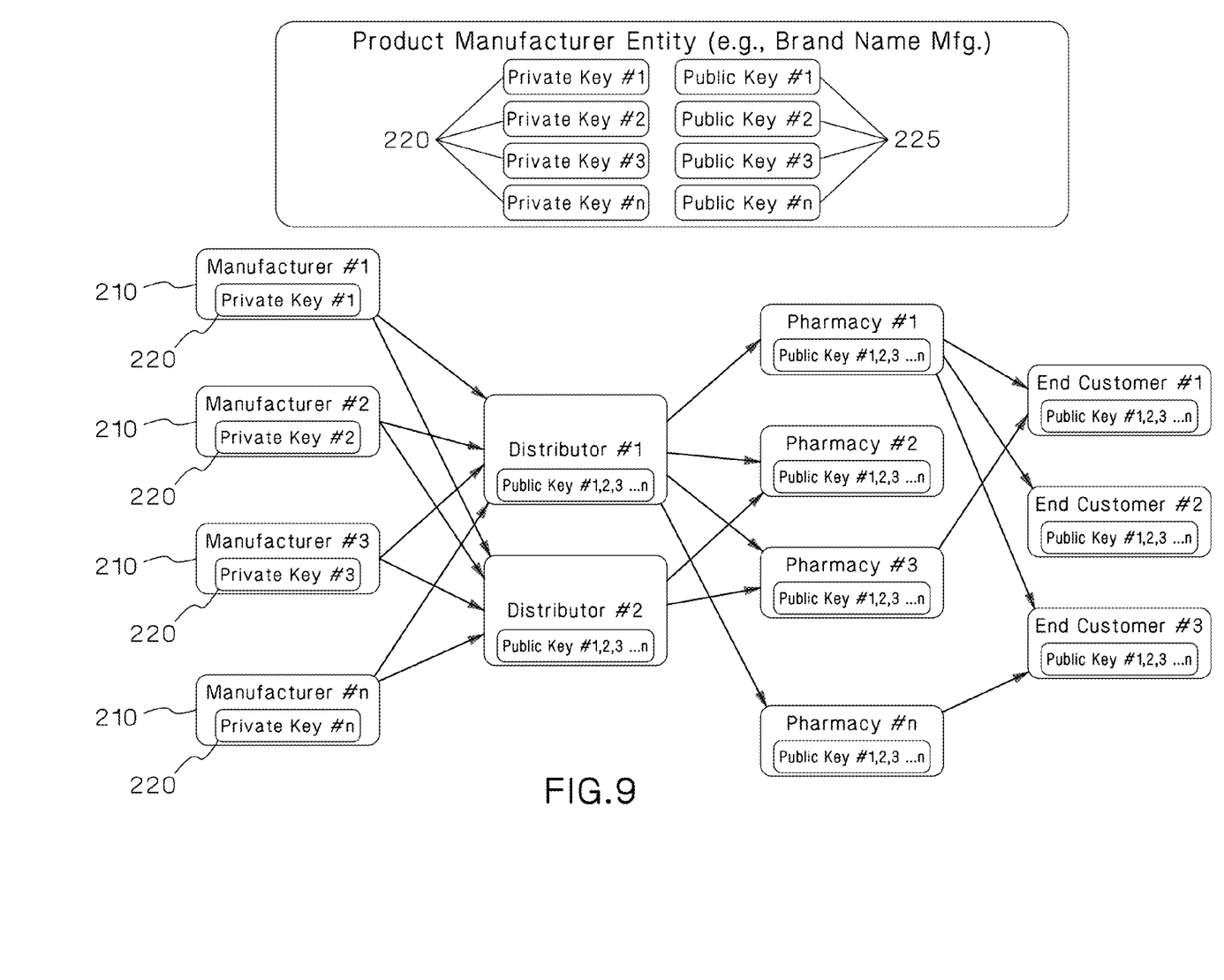
FIG. 9 shows a supply chain map according to another embodiment of the present invention where there is more than one OEM manufacturer.

Another embodiment where there is more than one OEM manufacturer is illustrated in FIG. 9. In this case, a unique private key 220 exists for every OEM manufacturer 210, where the private key security is managed by each respective manufacturer. In this embodiment, if there is a breach of security at one of the manufacturing facilities, only the one particular manufacturer could have counterfeiters, which limits the impact of a private key security breech. Correspondingly, the public sector would require as many public keys 225 as there are private keys 220.

In addition to providing product authentication, various aspects of the present invention may have a positive benefit where a particular product is stolen or otherwise misappropriated. For example, the entity from which a product was stolen can list the product's ID# in a national database, noting that this ID# is associated with a stolen product. When the stolen product is attempted to be brought back into the supply chain, the receiving entity (possibly another distributor, pharmacy, or an end customer), will have the opportunity to read the tag's supply chain information (if integrated into the original process), and determine if there was a supply chain violation or irregularity which would be a cause to make further inquires about the product's history (e.g., make a national database inquiry).

It should be noted that while this invention has been described in terms of one or more embodiment(s), these embodiment(s) are non-limiting, and there are alterations, permutations, and equivalents, which fall within the scope of this invention. It should also be noted that there are many alternative ways of implementing the methods and apparatuses of the present invention. It is therefore intended that claims that may follow be interpreted as including all such alterations, permutations, and equivalents as fall within the true spirit and scope of the present invention.

We claim:

1. A method against counterfeiting in a supply chain having a plurality of original equipment manufacturer (OEM) entities, each of said OEM entities manufacturing a plurality of units of a respective product, said method comprising the steps of:
    providing a plurality of radio-frequency identification (RFID) tags, each of said RFID tags having a unique identification string hardcoded therein and a user-accessible memory;
    having a process-controlling entity:
        asymmetrically encrypt by way of a private encryption key each of said unique identification strings to obtain respective authentication code words, each of said respective authentication code words corresponding to one of said respective unique identification strings;
        write each of said respective authentication code words into respective one of said user-accessible memory;
        divide said plurality of RFID tags into a plurality of batches, each of said plurality of batches having a respective plurality of OEM RFID tags, each of said plurality of batches corresponding to one of said plurality of OEM entities; and
        respectively distribute said plurality of batches to said plurality of OEM entities;
    having each of said plurality of OEM entities:
        attach each of said respective plurality of OEM RFID tags to one of said plurality of units of said respective product; and
        place said plurality of units of said respective product into said supply chain, said supply chain including at least one of a distributer and a retail location;
    reading at least one authentication code word and at least one respective unique identification string from at least one respective RFID tag attached to at least one respective unit, said reading occurring via an RFID reader at at least one of said distributer and said retail location;
    decrypting said read at least one authentication code word using a public decryption key to obtain a decrypted result; and
    comparing said decrypted result to said read at least one respective unique identification string, wherein said at least one respective unit is deemed genuine when said decrypted result matches said read at least one respective unique identification string and said at least one respective unit is deemed counterfeit when said decrypted result does not match said read at least one respective unique identification string.

2. The method of claim 1, wherein said respective product is a pharmaceutical drug.

3. The method of claim 1, wherein at least one of said provided plurality of RFID tags is tamperproof, said tamperproof RFID tag characterized by becoming disables if removed from a surface to which said tamperproof RFID tag is attached.

4. The method of claim 1, wherein at least one of said plurality of OEM entities, said distributer, and said retail location write supplemental data to at least one of said user-accessible memory.

5. A method against counterfeiting in a supply chain having a plurality of original equipment manufacturer (OEM) entities, each of said OEM entities manufacturing a plurality of units of a respective product, said method comprising the steps of:
    having a process-controlling entity manage a plurality of private encryption keys, each of said plurality of private encryption keys having a respective public decryption key, each of said plurality of private encryption keys corresponding to one of said plurality of OEM entities;
    providing a plurality of respective radio-frequency identification (RFID) tags to each of said plurality of OEM entities, each of said RFID tags having a unique identification string hardcoded therein and a user-accessible memory;
    having each of said plurality of OEM entities:
        asymmetrically encrypt by way of said respective private encryption key each of said respective unique identification strings to obtain respective authentication code words, each of said respective authentication code words corresponding to one of said respective unique identification strings;

write each of said respective authentication code words into respective one of said user-accessible memory;

attach each of said plurality of respective RFID tags to one of said plurality of units of said respective product; and place said plurality of units of said respective product into said supply chain, said supply chain including at least one of a distributer and a retail location;

reading at least one authentication code word and at least one respective unique identification string from at least one respective RFID tag attached to at least one respective unit, said reading occurring via an RFID reader at at least one of said distributer and said retail location;

decrypting said read at least one authentication code word using one of said respective public decryption keys to obtain a decrypted result; and comparing said decrypted result to said read at least one respective unique identification string, wherein said at least one respective unit is deemed genuine when said decrypted result matches said read at least one respective unique identification string and said at least one respective unit is deemed counterfeit when said decrypted result does not match said read at least one respective unique identification string.

6. The method of claim 5, wherein said respective product is a pharmaceutical drug.

7. The method of claim 5, wherein at least one of said provided plurality of respective RFID tags is tamperproof, said tamperproof RFID tag characterized by becoming disabled if removed from a surface to which said tamperproof RFID tag is attached.

8. The method of claim 5, wherein at least one of said plurality of OEM entities, said distributer, and said retail location write supplemental data to at least one of said user-accessible memory.

\* \* \* \* \*